United States Patent
Kosuri et al.

(10) Patent No.: US 10,988,805 B2
(45) Date of Patent: Apr. 27, 2021

(54) METHODS RELATED TO DNA SEQUENCING

(71) Applicant: The Regents of the University of California, Oakland, CA (US)

(72) Inventors: Sriram Kosuri, Los Angeles, CA (US); Rocky Cheung, Los Angeles, CA (US); Nathan B. Lubock, Monarch Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/552,040

(22) PCT Filed: Feb. 19, 2016

(86) PCT No.: PCT/US2016/018606
§ 371 (c)(1),
(2) Date: Aug. 18, 2017

(87) PCT Pub. No.: WO2016/134218
PCT Pub. Date: Aug. 25, 2016

(65) Prior Publication Data
US 2018/0037951 A1 Feb. 8, 2018

Related U.S. Application Data

(60) Provisional application No. 62/118,583, filed on Feb. 20, 2015.

(51) Int. Cl.
*C12Q 1/6874* (2018.01)
*C12Q 1/6869* (2018.01)
*C12N 15/10* (2006.01)

(52) U.S. Cl.
CPC ....... *C12Q 1/6874* (2013.01); *C12N 15/1065* (2013.01); *C12N 15/1082* (2013.01); *C12Q 1/6869* (2013.01)

(58) Field of Classification Search
CPC .......................... C12Q 1/6874; C12Q 1/6869; C12N 15/1065; C12N 15/1082
See application file for complete search history.

(56) References Cited

U.S. PATENT DOCUMENTS

| 2013/0017978 A1 | 1/2013 | Kavanagh et al. |
| 2013/0203605 A1 | 8/2013 | Shendure et al. |
| 2013/0252829 A1 | 9/2013 | Strathmann |

OTHER PUBLICATIONS

International Search Report and Written Opinion for International Application No. PCT/US2016/018606 dated Jun. 21, 2016.
Extended European Search Report issued by the European Patent Office in corresponding Application No. PCT/US2016/018606 dated Jun. 21, 2018.
EP Communication for EP Application No. 16753115.1 dated Jul. 3, 2019.
Hoess et al., "Mechanism of strand cleavage and exchange in the Cre-lox site-specific recombination system," Journal of Molecular Biology, 181(3):351-362 (1985).

*Primary Examiner* — Robert H Havlin
(74) *Attorney, Agent, or Firm* — Foley Hoag LLP

(57) ABSTRACT

In some aspects, the invention relates to a method for producing a barcoded DNA library, comprising: optionally fragmenting DNA to produce fragmented DNA; combining the DNA/fragments with control nucleotide sequences to produce a mixture of nucleic acids, each control nucleotide sequence comprising a variable nucleotide sequence, thereby barcoding the DNA/fragments; amplifying the mixture of nucleic acids to produce amplified nucleic acids; isolating a plurality of nucleic acids from the amplified nucleic acids; and rearranging the nucleic acids of the plurality, thereby producing the barcoded DNA library.

12 Claims, 4 Drawing Sheets
Specification includes a Sequence Listing.

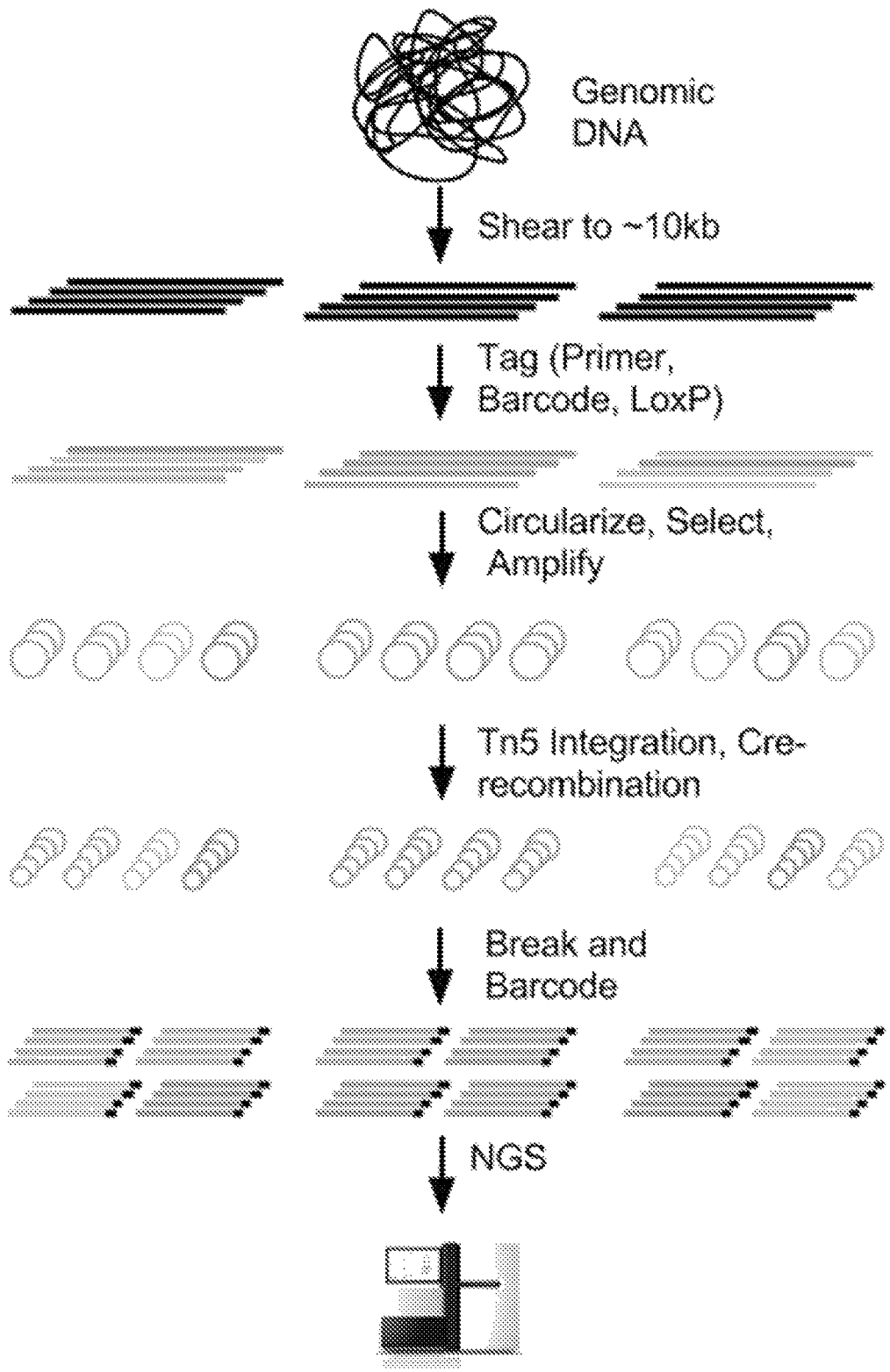

METHODS RELATED TO DNA SEQUENCING

RELATED APPLICATIONS

This application is a § 371 national-stage application based on PCT Application PCT/US16/018606, filed Feb. 19, 2016, which claims priority to U.S. Provisional Patent Application No. 62/118,583, filed Feb. 20, 2015, the specifications of both of which are hereby incorporated by reference herein in their entireties.

GOVERNMENT SUPPORT

This invention was made with Government support under GM114829, awarded by the National Institutes of Health. The Government has certain rights in the invention.

SEQUENCE LISTING

The instant application contains a Sequence Listing, which has been submitted electronically in ASCII format and is hereby incorporated by reference in its entirety. Said ASCII copy, created on Aug. 16, 2017, is named UCH-06601_SL.txt and is 760 bytes in size.

BACKGROUND

Long reads are critical for multiple applications that use Next-generation Sequencing (NGS). First, they allow long-range haplotyping, which is critical in understanding heredity factors resulting from genetic mutations. Second, they enable sequencing of repetitive regions and structural variants, which is difficult with short reads alone. Third, they allow for de novo sequencing of new organisms. Fourth, they provide much more useful results for metagenomic sequencing and screening heterogeneous mixtures of DNA (e.g., cancer genomes).

For this reason, several companies have focused on providing long read capabilities, and they are attempting to increase the read length through novel sequencing methods, but the error rates of their products are still too high for widespread use. Nevertheless, sequencers have been used in conjunction with short-read sequencers to finish a number of genomes. Others have attempted to increase the functional read length of existing NGS technologies for haplotyping applications through various barcoding strategies. However, these methods typically require that the sample be diluted and compartmentalized (often in 96 or 384 well plates) before it is barcoded in order to ensure that each barcoded piece of DNA is from a different chromosome. After barcoding, the sequences are typically amplified, sheared, and then sequenced.

These methods have shown some initial promise, but are highly optimized for haplotyping. Additionally, they involve an intensive library preparation, require a large excess of sequencing or show a significant PCR bias. Finally, none of these methods maintain contiguous coverage of the original piece of DNA, as the barcoding information is lost after fragmentation. New methods for barcoding and sequencing DNA would be beneficial for NGS technologies.

BRIEF DESCRIPTION

In some aspects, the invention relates to a method for obtaining a long consensus sequence from multiple short reads. Various methods of the invention are distinguished from existing technologies by using molecular recombination to bring a barcoded sequencing primer near a random stretch of DNA. Briefly, a large insert library that is barcoded with a "Barcoded Molecular Tag" may be employed. In some embodiments, the Barcoded Molecular Tag has several parts including a primer binding site, a molecular barcode, and a recombinase recognition site (e.g., LoxP, hix, LTR, FRT, VloxP, SloxP, rox, vox, or any mutant thereof) that together allow for our method to function. After amplification either in vivo or in vitro, a second recombinase recognition site may be inserted into a random location in the insert. The second recombinase site may be inserted by a transposase (e.g., Tn3, tn5, Tn7, Tn10, Tn903, Tn1682, Vibhar) or by other suitable methods that insert the second recombinase site at random (e.g., randomly cutting a DNA sequence and ligating a second recombinase site) A recombinase (e.g., Cre, Hin, Tre, Flp, VCre, SCre, Dre, or Vika) may then be used at low dilutions to facilitate intra-molecular recombination over inter-molecular, prior to preparing final libraries. Most importantly, the recombination brings a random location of a large insert next to a molecular barcode and sequencing primer, which allows a read of a particular insert molecule (identified by the barcode) into a random region of the insert. Examples of inserts include in vitro libraries of ~10 kb that can be amplified by rolling circle amplification or PCR, fosmid libraries of ~40 kb that can be selected and amplified by phage packaging and growth in *E. coli*, large 10-200 kb bacterial and yeast artificial chromosomes, or other suitable plasmid libraries.

DESCRIPTION OF THE FIGURES

FIG. 4. In some embodiments, the methods of the invention may be implemented entirely in vitro.

DETAILED DESCRIPTION

Barcoded Molecular Tag Design

Figure 1:
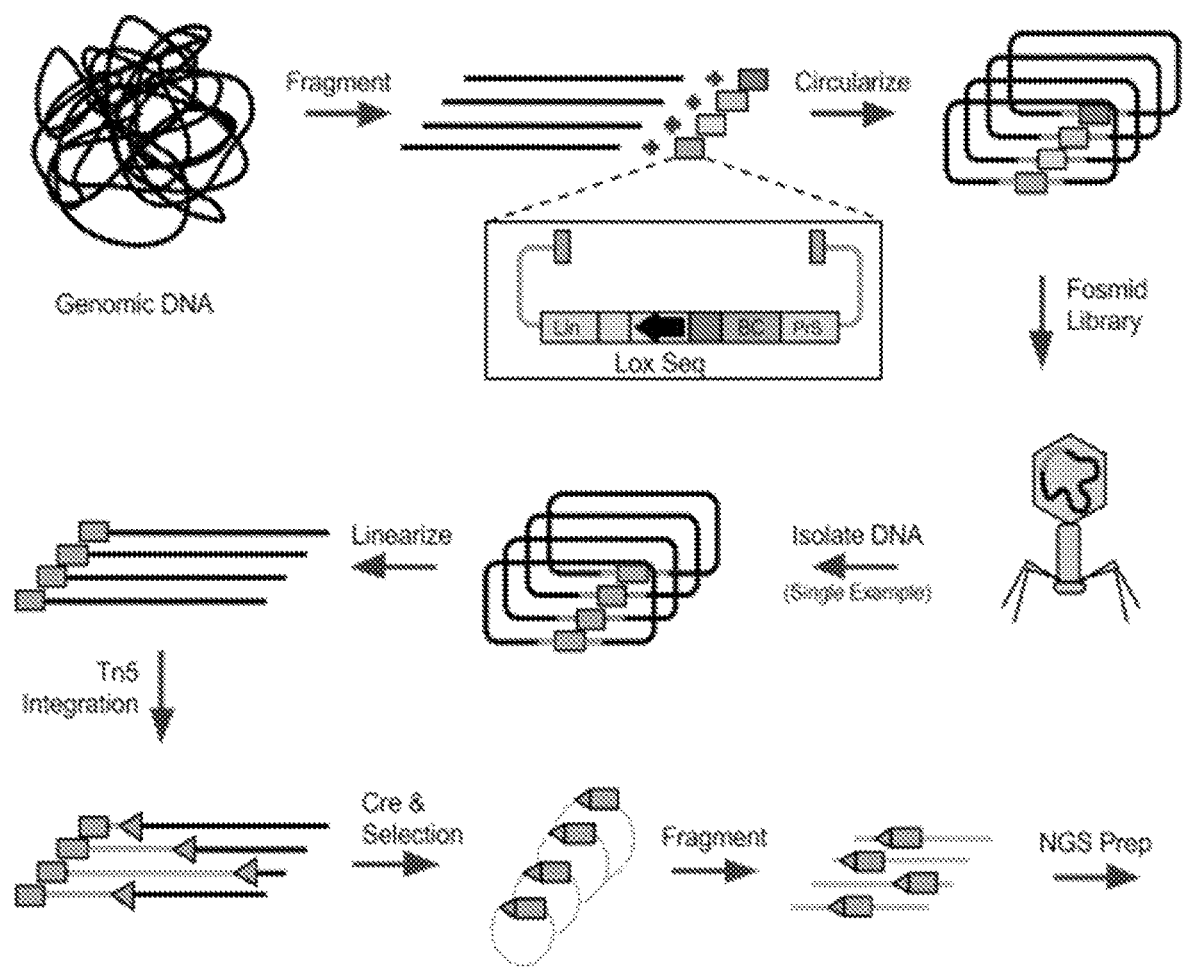
FIG. 1. Overview of some embodiments used for synthetic long reads using recombinase-assisted molecular barcoding. Genomic DNA is sheered and ligated to an engineered barcoded fosmid backbone that contains a first Lox sequence. These sequences are isolated and amplified by in vitro fosmid packaging and cloning into *E. coli*. The fosmids are linearized and Tn5 is used to integrate a second LoxP site. The DNA is incubated with Cre Recombinase to create circular DNA, which is enzymatically selected for by exonucleases. The library is fragmented and prepared for NGS using specific primers near the barcode. Finally, the DNA is sequenced and reads are assembled corresponding to each barcode.
Figure 2:
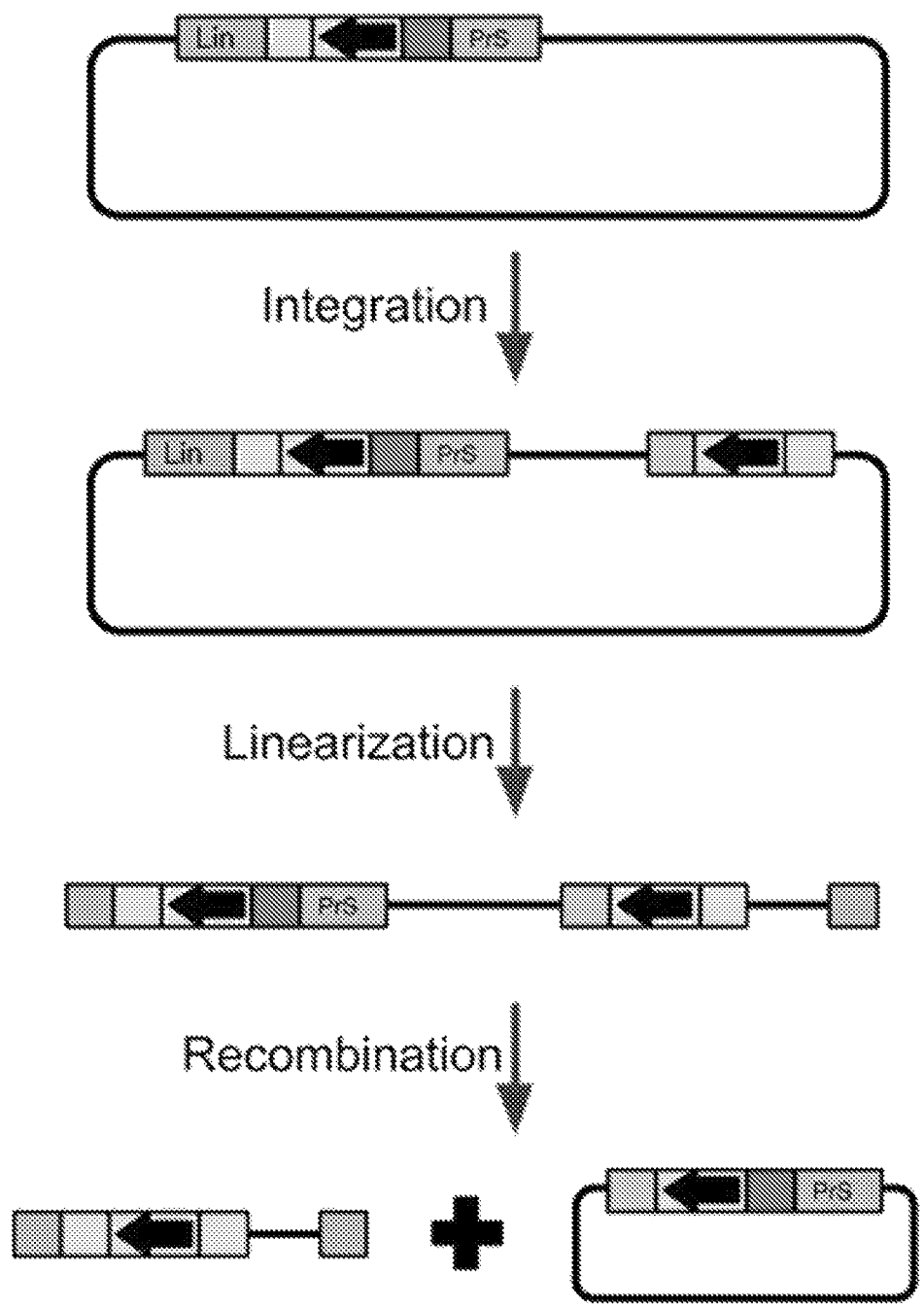
FIG. 2. In some embodiments, the orientation of a linearization sequence (Lin), sequencing primer (PrS), and loxP site on the barcoded tag is important to allow selection for circles in the experiments described in FIG. 1. The orientation allows the recombined region to be sequenced to occur within circular DNA, which can be selected for by exonuclease.
Figure 3:
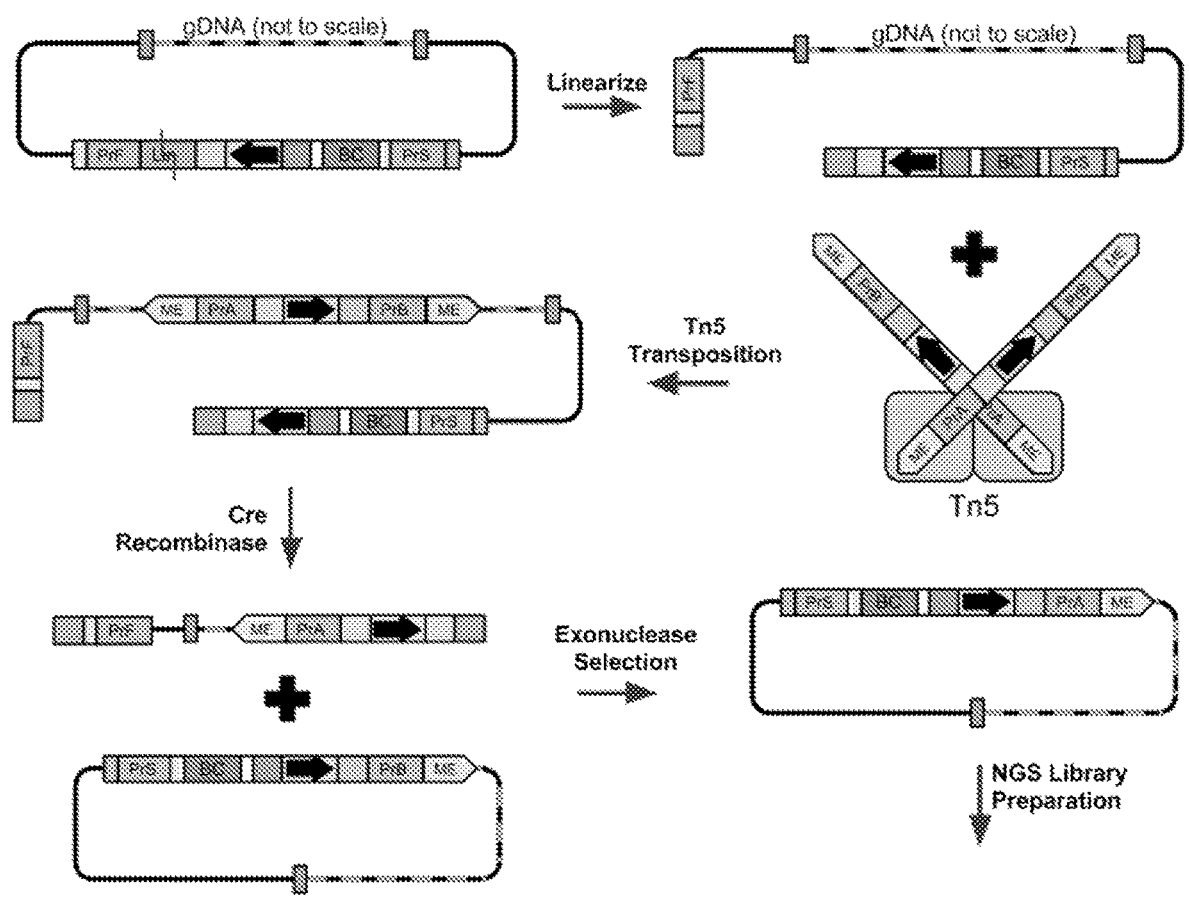
FIG. 3. A more detailed view of the linearization, transposition, recombination, and exonuclease selection events for the reaction scheme in FIG. 1.

In some embodiments, the Barcoded Molecular Tag contains a linearization sequence (to facilitate later selection of recombined circular DNA), a primer binding site for sequencing, a recombinase site (e.g., LoxP, hix, LTR, FRT, VloxP, SloxP, rox, vox, or any mutant thereof), and a barcode. The linearization site may be a rare-cutting homing endonuclease site, such as PI-PspI. In some embodiments, the geometry of the tag is important. In some preferred embodiments, the linearization sequence is located upstream of the recombinase site. If not, the sequencing primer will end up on the linear strand of DNA post-recombination, and the nucleic acids cannot be selected for by exonuclease digestion. In some preferred embodiments, the sequencing primer is designed such that it reads through the recombinase site upstream of it. This ensures that the nucleic acids are read from the tip of the second recombinase recognition site (e.g., LoxP, hix, LTR, FRT, VloxP, SloxP, rox, vox, or any mutant thereof) after recombination, and therefore any sequence in the proximity of where the second recombinase site was integrated. The recombinase may be Cre, Hin, Tre, Flp, VCre, SCre, Dre, or Vika. Finally, in some instances directional recombinase sites are employed, and in those cases the only recombinase recognition sequences with 5' mutations are preferably positioned downstream of the linearization sequence and upstream of the sequencing primer. This geometry ensures that the double mutant recombinase recognition (LoxP) sequence ends up in the circular DNA, thereby hindering any reverse reactions after Cre-mediated excision with a complimentary mutant recombinase sequence. This circularization upon recombinase allows for the selection of recombined molecules by enzymatically selecting for circular DNA using exonucleases. In preferred embodiments, the second recombinase site contains a label (e.g., biotin, desthiobiotin, or any analog thereof), thus allowing any sequence labeled with a label to be selected and sequenced. In some embodiments, a transposase which remains bound to DNA may be used to isolate species that have undergone transposition. The general strategies described above may be altered in many different ways; for example, in preferred embodiments, the recombined recombinase site may be used as a sequencing primer to avoid sequencing through the recombination site for each read, and resulting in shorter barcoded molecular tags. Additionally, the label may be any label capable of conjugating to a recombinase site without significantly affected recombinase-recombinant site interactions or recombinase activity.

In preferred embodiments, nucleic acids comprising a sequencing barcode may be cloned into a plasmid (e.g., pUC19 or fosmid) backbone. In preferred embodiments, plasmid libraries may be utilized to enable genome sequencing or generation of DNA barcode libraries. In other preferred embodiments, fosmid libraries may be utilized to enable genome sequencing or generation of DNA barcode libraries. Fosmid libraries provide a rapid way to clonally amplify libraries of ~40 kb constructs, and have been used to enable whole genome sequencing and haplotyping. The phage packaging step of Fosmid library preparation allows for the length of the inserts are fairly uniform, which aids downstream computational processing. Nevertheless, the sequencing method should work equally well for any long, circular DNA (e.g., bacterial artificial chromosomes) or even linear pieces of DNA, as long as they can be amplified sufficiently after the sequencing tag has been incorporated.
Mechanism Some of the methods described herein leverage molecular recombination between a constant tag and a randomly integrated probe to ensure that a barcoded sequencing primer is uniformly distributed throughout a given genomic sequence. This may be accomplished in three steps. First, the genomic sequence of interest and the constant sequencing tag (mentioned above) may be brought in proximity and amplified to a sufficient copy number. In some such embodiments, this step is accomplished by generating a fosmid library using a fosmid backbone that has an integrated Barcoded Molecular Tag. In other such embodiments, this step may be accomplished by generating a plasmid library using a plasmid vector that has an integrated Barcoded Molecular Tag. Second, a probe may be integrated into a random position into the newly generated copies. Here a transposase (e.g., Tn3, Tn5, Tn7, Tn9, Tn10, Tn903, or Tn1681) may be used to incorporate a second recombinase site into the fosmid or plasmid library and any number of alternate mechanisms could be used, including other transposon technologies, random opening of the DNA plasmid using nucleases and ligating a second recombinase site, and ligation of an adaptor. In some embodiments, the second recombinase site is conjugated to a label (e.g., biotin, desthiobiotin, or any analog thereof), therefore allowing selection of plasmids with both inverted and non-inverted integrated recombinase sites. In some embodiments, circular DNA may be selected, and thus the DNA may be linearized before the integration event, e.g., using a rare restriction enzyme cutter (homing endonuclease site). Third, the probe and the constant sequencing tag may be brought together through a recombination event. In this instance, since the starting material is linear, recombination produces a circular piece of DNA. As mentioned earlier, the geometry of the sequencing tag ensures that circularized constructs that contain the sequencing tag are selected. Circular nucleic acids may be selected using enzymatic methods, e.g., enzymes that digest linear DNA. Finally, the library may be sheared to a desired size, depending upon the sequencing platform, sequencing adaptors may be added to the DNA, and PCR may be used to amplify the barcoded molecular tags and/or the sequencing adaptor to produce a sequenceable library by next-generation sequencing.

In some aspects, the invention relates to a method for sequencing DNA, comprising combining DNA (e.g., fragmented DNA) with control nucleotide sequences to produce a mixture of nucleic acids; amplifying the mixture of nucleic acids to produce amplified nucleic acids; isolating a plurality of nucleic acids from the amplified nucleic acids; inserting a second recombinase recognition site into the nucleic acids of the plurality; incubating the plurality of nucleic acids with a recombinase under conditions that favor intramolecular rearrangement, thereby rearranging the nucleic acids of the plurality; and sequencing the nucleic acids of the plurality. Each control nucleotide sequence may comprise a primer binding sequence; a variable nucleotide sequence (e.g., a barcode sequence); and a first recombinase recognition site downstream from the variable nucleotide sequence. The different nucleic acids of the plurality may comprise different variable nucleotide sequences and different DNA sequences (e.g., from fragmented DNA). The second recombinase recognition site may be inserted into different locations in different nucleic acids of the plurality. In some embodiments, the variable nucleotide sequence is downstream from the primer binding sequence.

In some aspects, the invention relates to a method for producing a barcoded DNA library, comprising combining DNA (e.g., fragmented DNA) with control nucleotide sequences to produce a mixture of nucleic acids, thereby barcoding the DNA; amplifying the mixture of nucleic acids to produce amplified nucleic acids; isolating a plurality of nucleic acids from the amplified nucleic acids; and rearranging the nucleic acids of the plurality, thereby producing the barcoded DNA library. Each control nucleotide sequence may comprise a variable nucleotide sequence (e.g., a barcode sequence). The different nucleic acids of the plurality may comprise different variable nucleotide sequences and different DNA (such as DNA fragments). Each control nucleotide sequence may further comprise a first recombinase recognition site downstream from the variable nucleotide sequence, and the method may further comprise inserting a second recombinase recognition site into the nucleic acids of the plurality. The second recombinase recognition site may be inserted into different locations in different nucleic acids of the plurality; and rearranging the nucleic acids of the plurality may comprise incubating the plurality of nucleic acids with a recombinase under conditions that favor intramolecular rearrangement. Each control nucleotide sequence further comprises a primer binding sequence. The primer binding sequence may be upstream from the variable nucleotide sequence. The method may further comprise sequencing the nucleic acids of the plurality.

In some embodiments, the invention further comprises fragmenting DNA to produce the fragmented DNA. In some embodiments, the method does not comprise fragmenting the DNA, for example, for DNA that is already sized for next-generation sequencing. Thus, in some embodiments, "fragmented DNA" refers to a mixture of DNA that may not comprise fragments of genomic DNA. For example, fragmented DNA may refer to a mixture of plasmids, such as a mixture of linearized plasmids.

In some embodiments, sequencing comprises paired end sequencing. For example, nucleic acids of the plurality may be sequenced in two different directions.

The DNA may be genomic DNA, and may be of any origin, e.g., the DNA may be prokaryotic, such as bacterial DNA, or eukaryotic DNA, such as yeast or mammalian DNA, e.g., human DNA.

The control nucleotide sequence may further comprise an origin of replication, e.g., for amplification of the nucleotide sequences in bacteria or yeast.

In some embodiments, amplifying the mixture of nucleic acids comprises transforming host cells with the mixture of nucleic acids; and culturing the host cells, thereby amplifying the mixture of nucleic acids. The host cells may be, for example, bacterial cells or yeast cells. Transformation may comprise infecting cells with a virus, such as a phage.

Amplifying the mixture of nucleic acids may comprise rolling circle amplification, multiple displacement amplification, or PCR amplification.

Combining the fragmented DNA with control nucleotide sequences may comprise ligating the fragmented DNA with the control nucleotide sequences.

In some embodiments, the method further comprises digesting the plurality of nucleic acids with a restriction endonuclease after isolating the plurality of nucleic acids, wherein the control nucleotide sequences comprise a rare recognition site for a restriction endonuclease. The probability of finding the rare recognition site in a random nucleotide sequence of the same length as the recognition site may be less than one in one billion, such as less than 1 in $10^{10}$, less than 1 in $10^{11}$, less than 1 in $10^{12}$, less than 1 in $10^{13}$, less than 1 in $10^{14}$, less than 1 in $10^{15}$, less than 1 in $10^{16}$, less than 1 in $10^{17}$, less than 1 in $10^{18}$, less than 1 in $10^{19}$, or less than 1 in $10^{20}$. The probability of finding a rare recognition site in a random nucleotide sequence of the same length may be determined by calculating $4^n$, where 4 is the number of naturally occurring DNA bases and n is the length of the recognition site. For example, the PI-PspI recognition site is 30 bp long, and thus, the probability of finding a PI-PspI recognition site in a random 30 bp nucleotide sequence is approximately 1 in $10^{18}$ ($4^{30}=1.15\times10^{18}$). A rare recognition site may be selected based on the size of the DNA to be processed. For example, the human genome is approximately 3.3 billion base pairs, and thus, a rare recognition site may be selected that occurs less than once in 3.3 billion random nucleotide sequences of the same length when processing human genomic DNA, such as a recognition site that occurs less than once in $10^{11}$ random nucleotide sequences, or more preferably less than once in $10^{12}$ random nucleotide sequences.

In some embodiments, the recombinase is Cre recombinase and the first and second recombinase recognition sites are loxP sites (e.g., mutated loxP sites). Inserting a second recombinase recognition site may comprise incubating the plurality of nucleic acids with a second control nucleic acid and a transposase, the second control nucleic acid comprising the second recombinase recognition site and a transposable element. In some embodiments, the recombinase is Hin recombinase and the first and second recombinase recognition sites are hix sites. In some embodiments, the recombinase is Tre recombinase and the first and second recombinase recognition sites are LTR sites. In some embodiments, the recombinase is VCre recombinase and the first and second recombinase recognition sites are VloxP sites. In some embodiments, the recombinase is SCre recombinase and the first and second recombinase recognition sites are SloxP sites. In some embodiments, the recombinase is Dre recombinase and the first and second recombinase recognition sites are rox sites. In some embodiments, the recombinase is Vika recombinase and the first and second recombinase recognition sites are vox sites. In some embodiments, the recombinase is FLP recombinase and the first and second recombinase recognition sites are FRT sites. Inserting a second recombinase recognition site may comprise incubating the plurality of nucleic acids with a second control nucleic acid and a transposase, the second control nucleic acid comprising the second recombinase recognition site and a transposable element. The transposase can be a Tn3, Tn5, Tn7, Tn9, Tn10, Tn903, or a Tn1681 transposase. In some embodiments, the second recombinase recognition site is conjugated to a label (e.g., biotin, desthiobiotin, or any analog thereof).

In some embodiments, rearranging the nucleic acids of the plurality comprises incubating with plasmids with functionalized beads that recognize the label (e.g., comprising conjugated streptavidin moieties). Incubation with functionalized beads allows the isolation of species that have undergone recombination. In some embodiments, rearranging the nucleic acids of the plurality comprises random endonuclease cleavage or exonuclease digestion. Rearranging the nucleic acids may comprise ligation of the second recombinase recognition site. Similarly, rearranging the nucleic acids of the plurality may comprise limited digestion of the nucleic acids of the plurality with a common restriction endonuclease, e.g., followed by ligation of the second recombinase recognition site.

In some embodiments, sequencing the nucleic acids of the plurality comprises sequencing the nucleic acids with a primer that binds to the second recombinase recognition site.

In some aspects, the invention relates to a plurality of nucleic acids, each nucleic acid comprising a primer binding sequence; a variable nucleotide sequence downstream from the primer binding sequence (e.g., a barcode sequence); a first recombinase recognition site downstream from the variable nucleotide sequence; and DNA (e.g., from a sample of interest, such as fragmented DNA). The different nucleic acids of the plurality may comprise different variable nucleotide sequences and different DNA sequences (e.g., DNA fragments). DNA fragments may comprise genomic DNA fragments. The DNA (e.g., fragmented DNA) may be downstream from the first recombinase recognition site.

Each nucleic acid may further comprise a rare recognition site for a restriction endonuclease. The probability of finding the rare recognition site in a random nucleotide sequence of the same length as the recognition site may be less than one in one billion such as less than 1 in $10^{10}$, less than 1 in $10^{11}$, less than 1 in $10^{12}$, less than 1 in $10^{13}$, less than 1 in $10^{14}$, less than 1 in $10^{15}$, less than 1 in $10^{16}$, less than 1 in $10^{17}$, less than 1 in $10^{18}$, less than 1 in $10^{19}$, or less than 1 in $10^{20}$.

In some embodiments, a portion of the plurality of nucleic acids further comprises a second recombinase recognition site, wherein the second recombinase recognition site is present at different locations in different nucleic acids of the plurality.

In some aspects, the invention relates to a kit for accomplishing the methods described herein. In some embodiments, the kit comprises control nucleotide sequences, each control nucleotide sequence comprising a primer binding sequence a variable nucleotide sequence (e.g., a barcode sequence) downstream from the primer binding sequence; and a first recombinase recognition site. The first recombinase recognition site of each control nucleotide sequence may be located downstream from each variable nucleotide sequence.

In some aspects, the invention relates to a plasmid comprising a primer binding sequence, a variable nucleotide sequence downstream from the primer binding sequence, and a first recombinase recognition site downstream from the variable nucleotide sequence. In some embodiments, the plasmid further comprises a second recombinase recognition site.

In some such embodiments, the plasmid comprises a label (e.g., biotin, desthiobiotin, or any analog thereof) coupled to the second recombinase recognition site.

This disclosure will be better understood from the Experimental Details which follow. However, one skilled in the art will readily appreciate that the specific methods and results discussed are merely illustrative of the disclosure as described more fully in the embodiments which follow thereafter.

EXEMPLIFICATION

Example 1: Representative Sequencing Method

Plasmid Cloning and Addition of Barcode

An un-barcoded version of our sequencing tag (sequencing primer, a mutant LoxP site (Jtz17), and linearization sequence (PI-pspI), ordered from IDT as a g-block) was cloned into a modified pUC19 vector containing an XhoI site. Vector was digested with AatII, XhoI, and DpnI and the insert was digested with AatII and XhoI in separate vessels, followed by heat inactivation of the enzymes. Next, the vector and insert were ligated with T4 DNA ligase for 15 min at 23° C. The products were then purified with a Qiagen PCR Purification Kit. Products were transformed into NEB 5-alpha C2987H chemical competent cells. Using a sequence verified clone, the plasmid was cleaved via PCR and ligated with yeast gDNA. Yeast gDNA was purified from *S. cerevisiae* with the MasterPure Yeast DNA Purification Kit (EpiBio), sheared to ~1.5 kb with a Covaris m220, and end repaired with Enzymatic's End Repair Kit. Ligation products were transformed into NEB 5-alpha C2987H chemical competent cells. After selecting a sequence-verified clone, a barcode was added in between the sequencing primer and the recombinase site with PCR. The primers contained an orthogonal cut site, NheI, to allow for more efficient re-ligation. Following incubation of PCR products with NheI, the product were then re-circularized them with T4 DNA ligase for 15 minutes at 23 C, and cloned the ligated products into NEB 5-alpha C2987H chemical competent cells. Finally, plasmid DNA was prepared from the liquid culture resulting in our final barcoded library.

Tn5 Transposition, Cre Recombination, and Next Generation Sequencing (NGS) Library Preparation Tn5 was used to integrate a second mutant LoxP site, Jt15, into our plasmid library. Jt15 was flanked by two primers for downstream amplification and was ordered as a g-block from IDT. The sequence was verified via TOPO-cloning. Jt15 and 852 bases of the TOPO backbone was amplified using primers with ME sequence overhangs. An optional step included amplifying Jt15 with extra bases so Tn5 insertions could be visualized with a gel shift assay.

The plasmid library and the Jt15 recombinase site with overhang were incubated in a 1:1 molar ratio in the presence of Tn5 for 2 hours at 37 C. After heat inactivation for 10 minutes at 70 C and incubation with ~0.01% SDS (final volume), the products were incubated with 1.8×SPRI beads to clean and concentrate our DNA. DNA (~1 ug) was then incubated with Cre recombinase (NEB, 150 nM) with our DNA for 30 minutes at 37 C, and 10 minutes at 70 C for heat inactivation. Again, products were cleaned with 1.8×SPRI beads. The recombined products were fragmented and amplified using a home-made Nextera mix. Tn5 transposase and tagmentation procedures for massively scaled sequencing projects *Genome Res.* 24:2033-2040, hereby incorporated in its entirety. Libraries were quantified using the Kapa Library Quantification Kit and sequenced using an Illumina MiSeq Nano v2 PE150 kit. Any NGS preparation kit will suffice here.

Tn5 Purification

All Tn5 used in these experiments were purified as explained in Picelli et al. (2014) Tn5 transposase and tagmentation procedures for massively scaled sequencing projects. *Genome Res.* 24:2033-2040, hereby incorporated by reference herein in its entirety. More information and examples of mutations that increase Tn5 activity, Tn5's role in transposition, and the fragmentation step used in Next Generation Sequencing can be found in U.S. Pat. No. 7,083,980, WO1998010077, U.S. Pat. No. 9,080,211, and WO2015160895, hereby incorporated by reference herein in their entirety.

Example 2, and all of the methods disclosed therein, is prophetic.

Example 2: Representative Sequencing Method Using Fosmid Cloning

Preparation of the Fosmid Control Nucleotide Sequence

The endogenous LoxP site on EpiCentre's fosmid vector (pCC2FOS) is removed to eliminate any spurious interactions with the engineered LoxP sites. Since pCC2FOS is supplied blunted and dephosphorylated, the vector is re-phosphorylated with T4 polynucleotide kinase and re-ligated with T4 ligase. The pCC2FOS vector is purified and transformed into NEB 5-alpha C2987H chemical competent cells. The transformed cells are grown overnight at 37° C. in Luria-Bertani (LB) medium with 12.5 µg/mL chloramphenicol (Cm). The cells are screened for blue colonies on LB agar plates with 20 µg/mL X-Gal and 100 µM IPTG. The blue colonies are grown overnight in 10 mL LB and pCC2FOS is extracted with a Qiagen Mini-prep kit. The presence of pCC2FOS is confirmed by electrophoresis on an agarose gel.

The endogenous LoxP site is removed from the re-circularized pCC2FOS vector via PCR amplification. The resulting PCR products are purified with a Qiagen PCR Purification Kit. The size of the vector is confirmed by agarose gel electrophoresis.

```
Forward Primer EpiBio (AatII)
                                    SEQ ID NO: 1
ATGCGACGTCTGGCTTAACTATGCGGCATC Reverse Primer EpiBio (XhoI)
                                    SEQ ID NO: 2
ATGCCTCGAGATTAGCGATGAGCTCGGACT
```

Incorporation of the Sequencing Tag

When deleting the endogenous LoxP site pCC2FOS, orthogonal restriction enzyme sites (AatII and XhoI) are added to the primers. This ensures that the vector can be easily re-circularized as well as combined with any sequence of interest. In particular, a sequencing tag is incorporated, which was ordered from IDT as a g-block. First, the vector was digested with AatII, XhoI, and DpnI and the insert was digested with AatII and XhoI in separate vessels, followed by heat inactivation of the enzymes. Next, the vector and insert are incubated with T4 DNA ligase for 15 min at 23° C. The recircularized pCC2FOS with additional sequencing tag (pBag) is purified with a Qiagen PCR Purification Kit and transformed into NEB 5-alpha C2987H chemical competent cells. The transformed cells are screened blue colonies as above and the insert is confirmed by colony PCR (NEB Q5 Polymerase).

Addition of the Barcode

In some embodiments, each piece of DNA must have a unique barcode. To facilitate library creation, the sequencing tag is engineered to have an orthogonal restriction enzyme site (NheI) that generates compatible "sticky-ends" during digestion. By digesting the insert with restriction enzymes that generate complementary "sticky-ends" (in this case XbaI and SpeI), and subsequently incubating with all three enzymes during the ligation step, the background noise created by plasmids that re-ligate with themselves is reduced.

To accomplish this, NEB 5-alpha C2987H chemical competent cells containing the un-barcoded pBag vector are grown overnight in LB as above. The pBag vectors (pCC2FOS with sequencing tag) are then purified with a Qiagen Mini-prep kit. The barcodes (with primer and restriction enzyme sites) are oligonucleotides ordered from IDT with hand mixed bases at equal frequencies for A, T, G, and C. The barcodes are amplified via PCR (NEB Q5 Polymerase.

The vector is digested with NheI (NEB) and the insert is digested with XbaI and SpeI in separate vessels, followed by heat inactivation of the enzymes. Next, the vector and insert are incubated with T4 DNA ligase in the presence of NheI, XbaI, and SpeI. Frozen aliquots of the purified, barcoded library are saved for future experiments.

Genomic DNA Isolation

High molecular weight genomic DNA (HMW gDNA) from *Saccharomyces cerevisiae* is isolated with the MasterPure Yeast DNA Purification Kit (EpiBio). The genomic DNA is randomly sheared the by passing it through a 200 µL pipette tip ~75 times. The size range of the HMW gDNA is assessed via pulsed-field gel electrophoresis (PFGE). After gel isolating sheared gDNA of ~40 kb, an end-repair reaction was performed. The size of the end-repaired DNA is confirmed by PFGE, and ~40 kb end-repaired fragments are purified with an EpiCentre gel extraction kit.

Fosmid Library Creation

The end-repaired gDNA is combined with the barcoded library using blunt cloning. First, the gDNA is incubated with the barcoded pBag library and PmeI (NEB), followed by a heat inactivation of the enzyme. Next, the vector is dephosphorylated with calf intestinal alkaline phosphatase (CIP). Following the CIP treatment, the gDNA is ligated into the blunted and dephosphorylated vector with an EpiCentre ligation kit. The fosmid library is created according to the CopyControl fosmid library kit (EpiCentre). Briefly, the ligated DNA is packaged into phage used to infect EPI300-T1$^R$ cells. These cells are grown overnight and blue colonies are selected as above.

Second LoxP Integration

In order to sequence the fosmid library, a second LoxP site is incorporated. The LoxP site (as well as mutants Lox71 and JTZ15) is flanked by primers, and is ordered as oligonucleotides from IDT. The oligonucleotides are cloned into pUC19 using a Qiagen Topo-Clone Kit, and the resultant vector is transformed into host cells. The cells are grown in Kanamycin selective media and the sequence of the LoxP sites is verified via colony PCR and Sanger Sequencing. After sequence verification, the LoxP sites are amplified via PCR. In addition, the primers used during this amplification step contain the mosaic end (ME) sequences that are recognized by Tn5 transposase. The resulting amplicons are purified with a Qiagen PCR clean-up kit and froze aliquots are stored for future use.

In order to ensure there is ample vector, over-expression of the fosmid library is induced with the manufacturer's supplied Autoinduction Solution according to the manufacturer's specifications (EpiCentre). The fosmid library is subsequently purified with the FosmidMAX DNA purification kit form EpiCentre according to the manufacturer's specifications. With both the insert and fosmid library prepared, the transposition is performed in vitro with Tn5 transposase according to the manufacturer's specifications (EpiCentre). After adding 1% SDS and heat inactivating for 10 mins at 70° C. to halt the transposition, the resulting products are purified with a Qiagen PCR clean-up kit.

Cre Recombination

It is advantageous to linearize the fosmid vector as this allows for selection before recombination. Thus, a homing endonuclease site is included in the sequencing tag of the pBag vector. The PI-PspI (NEB) may be utilized for yeast genomic DNA, and other homing endonuclease sites can be used as needed. The fosmid library (with second LoxP site) is incubated with the homing endonuclease PI-PspI. Since PI-PspI cannot be heat inactivated without denaturing the DNA, 0.5% SDS was used to disrupt enzymatic activity. The linearized fosmid library was the purified with a phenol/chloroform extraction followed by ethanol precipitation.

Next, the purified product is incubated with Cre Recombinase for 20 min at 37° C. followed by a head inactivation step for 10 min at 70° C. The library is optionally purified. After recombination, circular constructs are selected by incubating with T5 exonuclease for 30 min at 37° C. Since T5 exonuclease cannot be heat inactivated, a phenol/chloroform extraction followed by ethanol precipitation is used to purify the circular DNA.

Next-Generation Sequencing Library Preparation

Circular constructs to ~600 bp are prepared by hydroshear. Then, the Illumina TruSeq Library Preparation Kit is used to prepare the DNA for NGS. Instead of amplifying on the canonical Illumina primers, the sequencing primers contained in the sequencing tag may be used to amplify the DNA for sequencing.

INCORPORATION BY REFERENCE

All of the U.S. patents, U.S. published patent applications, foreign patent publications, and other publications cited herein are hereby incorporated by reference.

EQUIVALENTS

Those skilled in the art will recognize, or be able to ascertain using no more than routine experimentation, many equivalents to the specific embodiments of the invention described herein. Such equivalents may have the following characteristics.

What is claimed:

1. A method for producing a barcoded DNA library for obtaining a consensus sequence from multiple short reads by using molecular recombination to bring a barcoded sequence near a random stretch of DNA, comprising:
   combining DNA with control nucleotide sequences to produce a mixture of nucleic acids, each control nucleotide sequence comprising, a primer binding site, a variable nucleotide sequence, and a first recombinase recognition site downstream from the primer binding site, and the variable nucleotide sequence, thereby barcoding the DNA;
   amplifying the mixture of nucleic acids to produce amplified nucleic acids;
   isolating a plurality of nucleic acids from the amplified nucleic acids, wherein different nucleic acids of the plurality comprise different variable nucleotide sequences and different DNA fragments;
   inserting a second recombinase recognition site into the nucleic acids of the plurality, wherein the second recombinase recognition site is inserted into a location that varies among separate individual nucleic acids of the plurality; and
   rearranging the nucleic acids of the plurality, thereby producing the barcoded DNA library.

2. The method of claim 1, wherein the DNA is fragmented DNA.

3. The method of claim 1, wherein rearranging the nucleic acids of the plurality comprises incubating the plurality of nucleic acids with a recombinase under conditions that favor intramolecular rearrangement.

4. The method of claim 3, wherein the recombinase is selected from the group consisting of:
   Cre recombinase and the first and second recombinase recognition sites are loxP sites;
   Flp recombinase and the first and second recombinase recognition sites are FRT sites; and
   Tre recombinase and the first and second recombinase recognition sites are LTR sites.

5. The method of claim 1, wherein the second recombinase recognition site is conjugated to a label.

6. The method of claim 1, wherein inserting a second recombinase recognition site comprises incubating the plurality of nucleic acids with a second control nucleic acid and a transposase, the second control nucleic acid comprising the second recombinase recognition site and a transposable element.

7. The method of claim 6, wherein the transposase is Tn3 transposase, Tn5 transposase, Tn7 transposase, Tn9 transposase, Tn10 transposase, Tn903 transposase, or Tn1681 transposase.

8. The method of claim 1, wherein each control nucleotide sequence comprises a primer binding sequence upstream from the variable nucleotide sequence.

9. The method of claim 1, further comprising sequencing the nucleic acids of the plurality.

10. The method of claim 1, wherein the control nucleotide sequence further comprises an origin of replication.

11. The method of claim 10, wherein amplifying the mixture of nucleic acids comprises:
   transforming host cells with the mixture of nucleic acids; and
   culturing the host cells, thereby amplifying the mixture of nucleic acids.

12. The method of claim 10, wherein amplifying the mixture of nucleic acids comprises rolling circle amplification or multiple displacement amplification.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgcgacgtc tggcttaact atgcggcatc                                      30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgcctcgag attagcgatg agctcggact                                      30